US012673317B2

(12) United States Patent
Ansovini et al.

(10) Patent No.: US 12,673,317 B2
(45) Date of Patent: Jul. 7, 2026

(54) PROCESS FOR RECOVERING AND REGENERATING A CATALYST FROM ASH

(71) Applicant: Avantium Knowledge Centre B.V., Amsterdam (NL)

(72) Inventors: Davide Ansovini, Amsterdam (NL); Benjamin McKay, Amsterdam (NL); Jagdeep Singh, Amsterdam (NL)

(73) Assignee: Avantium Knowledge Centre B.V., Amsterdam (NL)

( * ) Notice: Subject to any disclaimer, the term of this patent is extended or adjusted under 35 U.S.C. 154(b) by 607 days.

(21) Appl. No.: 18/027,808

(22) PCT Filed: Sep. 27, 2021

(86) PCT No.: PCT/EP2021/076508
§ 371 (c)(1),
(2) Date: Mar. 22, 2023

(87) PCT Pub. No.: WO2022/064039
PCT Pub. Date: Mar. 31, 2022

(65) Prior Publication Data
US 2023/0330643 A1 Oct. 19, 2023

(30) Foreign Application Priority Data
Sep. 28, 2020 (EP) ..................................... 20198772

(51) Int. Cl.
| | |
|---|---|
| *B01J 23/92* | (2006.01) |
| *B01J 23/30* | (2006.01) |
| *B01J 38/52* | (2006.01) |
| *B01J 38/60* | (2006.01) |
| *C07C 29/60* | (2006.01) |

(52) U.S. Cl.
CPC .............. *B01J 23/92* (2013.01); *B01J 23/30* (2013.01); *B01J 38/52* (2013.01); *B01J 38/60* (2013.01); *C07C 29/60* (2013.01)

(58) Field of Classification Search
CPC ... B01J 23/30; B01J 23/92; B01J 38/52; B01J 38/60; C07C 29/60
See application file for complete search history.

(56) References Cited

FOREIGN PATENT DOCUMENTS

| | | | | |
|---|---|---|---|---|
| CN | 106830087 A | * | 6/2017 | ............. C01B 3/042 |
| CN | 109248678 A | * | 1/2019 | ............. B01J 23/31 |
| CN | 106866372 B | | 8/2020 | |

(Continued)

OTHER PUBLICATIONS

Tai, Zhijun, et al. "Catalytic conversion of cellulose to ethylene glycol over a low-cost binary catalyst of Raney Ni and tungstic acid." ChemSusChem 6.4 (2013): 652-658.*

(Continued)

*Primary Examiner* — Richard M Rump
(74) *Attorney, Agent, or Firm* — Suiter Swantz IP

(57) ABSTRACT

A process for recovering and regenerating a tungsten compound suitable as co-catalyst in converting carbohydrates with hydrogen into alkylene glycols and polyols, from ash comprising one or more tungsten-oxygen components (e.g. comprising a tungstate and/or tungstic acid). Such ash is obtainable from burning a liquid mixture comprising alkylene glycols and/or polyols and sodium tungstate and/or tungstic acid.

12 Claims, 3 Drawing Sheets

(closed circles relate to P101, closed triangles relate to P039)

(56) References Cited

FOREIGN PATENT DOCUMENTS

| WO | 2016114661 | A1 | 7/2016 |
| WO | 2017042125 | A1 | 3/2017 |

OTHER PUBLICATIONS

English machine translation of 10924867A. (Year: 2019).*
English machine translation of CN106830087A. (Year: 2017).*
International Search Report and Written Opinion mailed Jan. 5, 2022 for PCT/EP2021/076508.

* cited by examiner

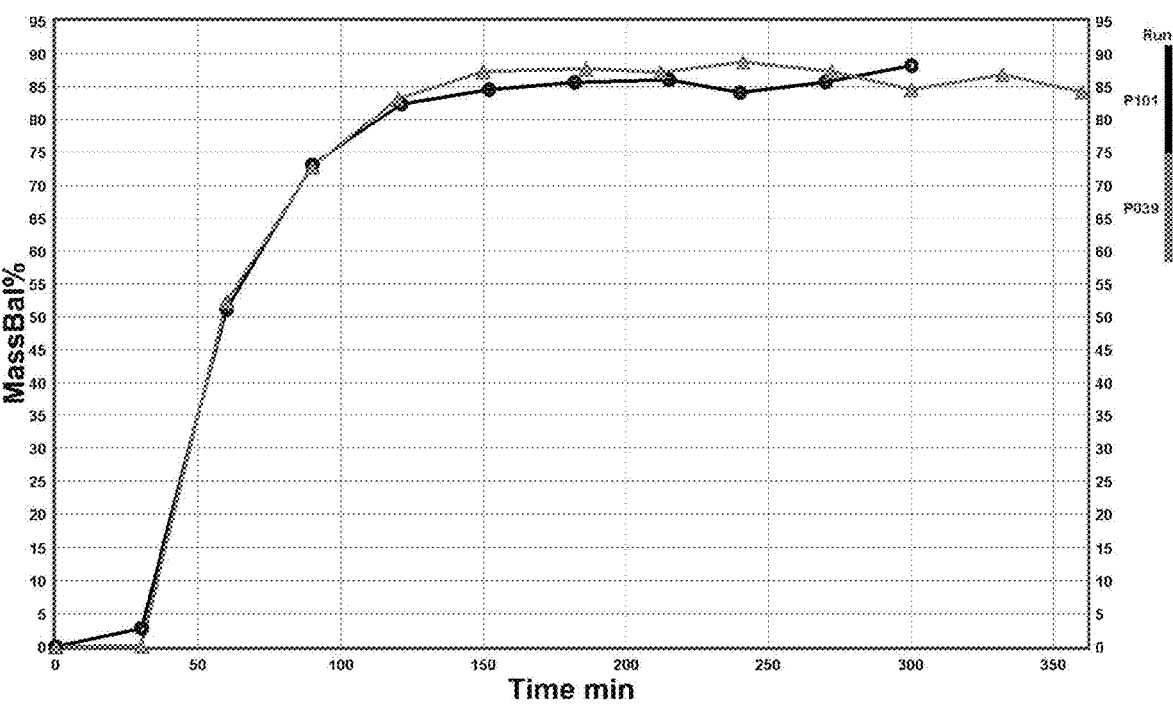
Figure 1 (closed circles relate to P101, closed triangles relate to P039)
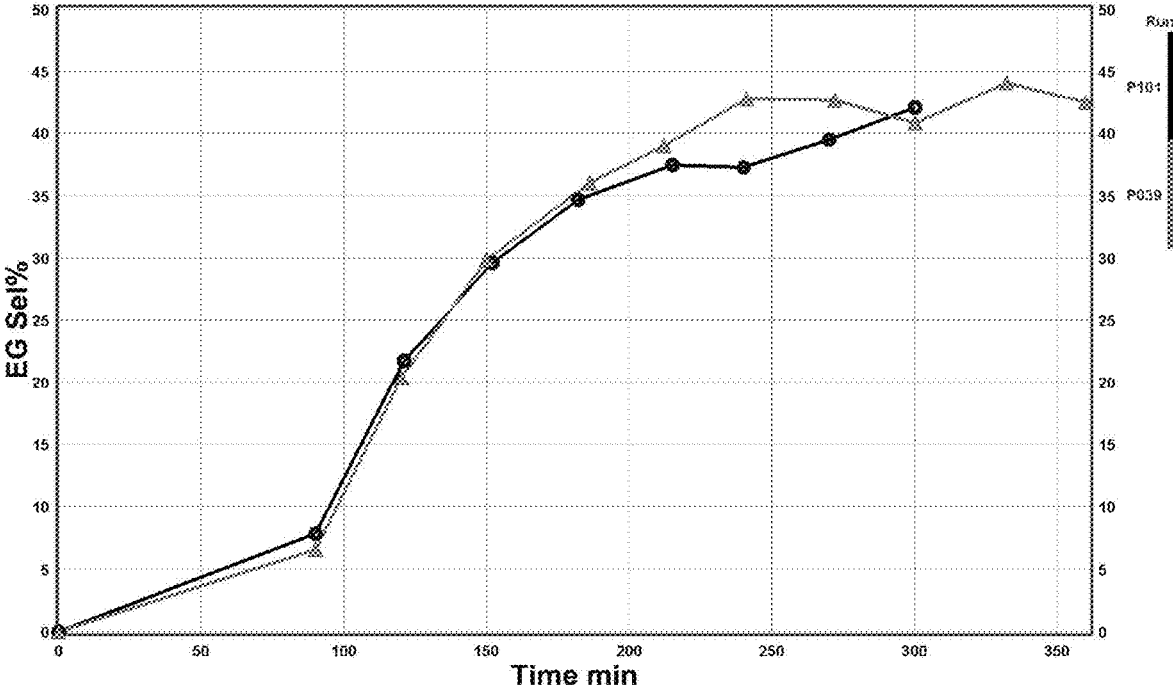
Figure 2 (closed circles relate to P101, closed triangles relate to P039)

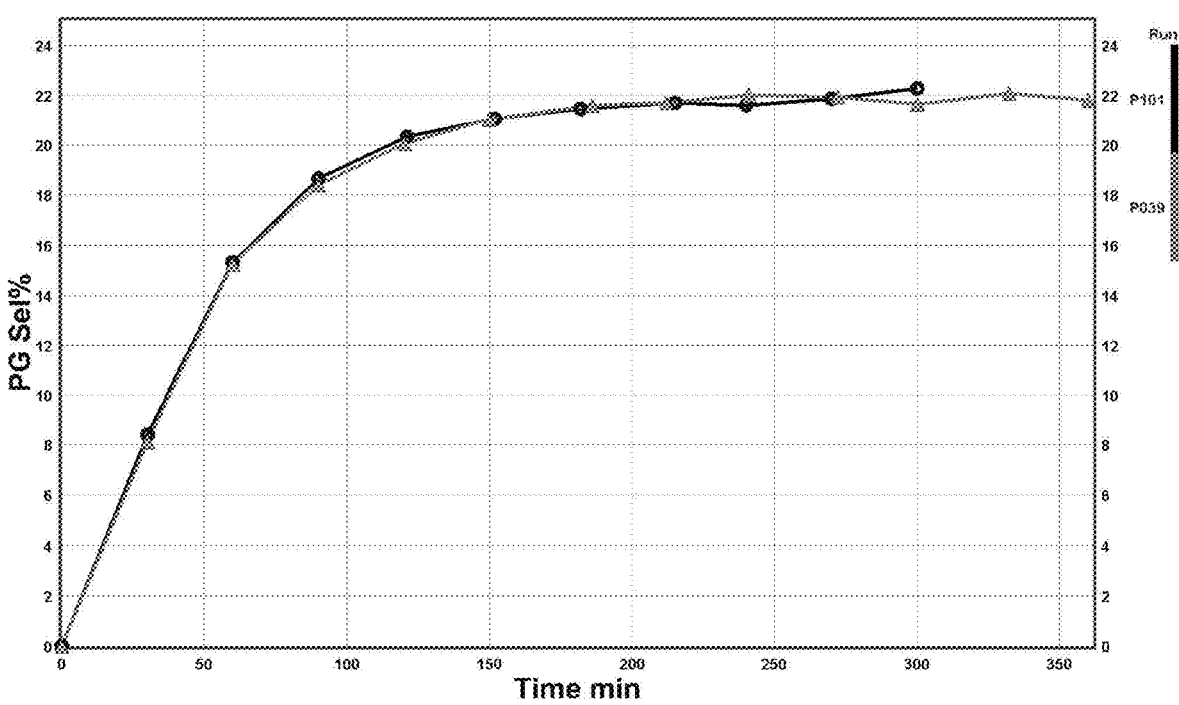
Figure 3 (closed circles relate to P101, closed triangles relate to P039)
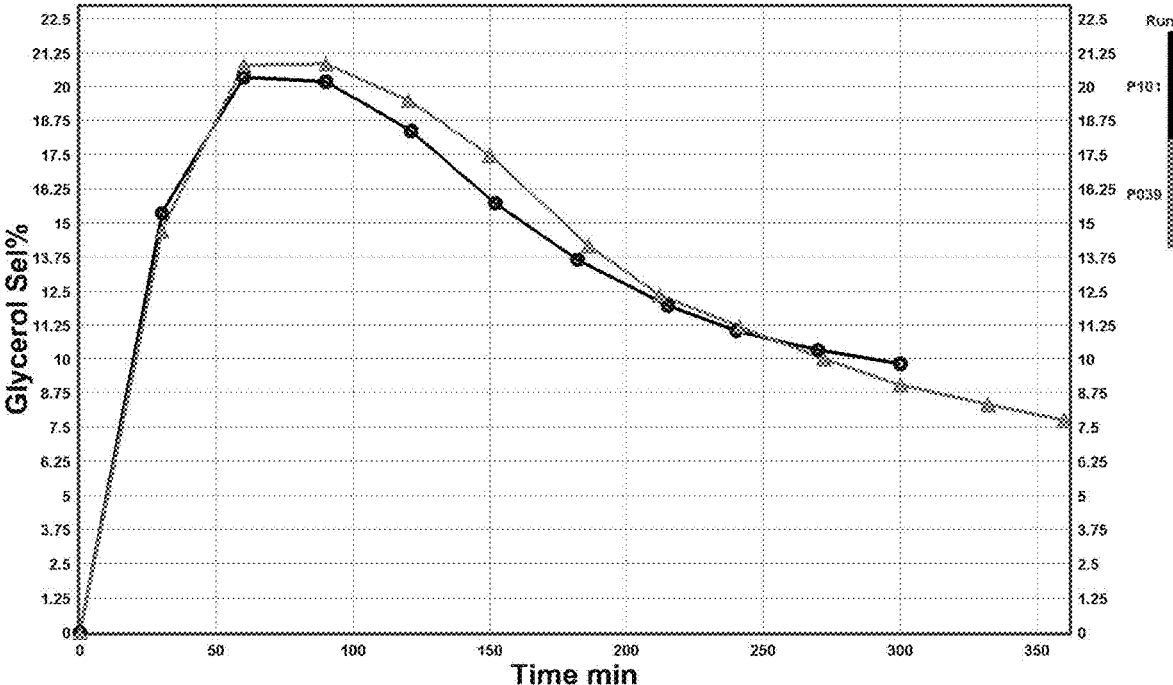
Figure 4 (closed circles relate to P101, closed triangles relate to P039)

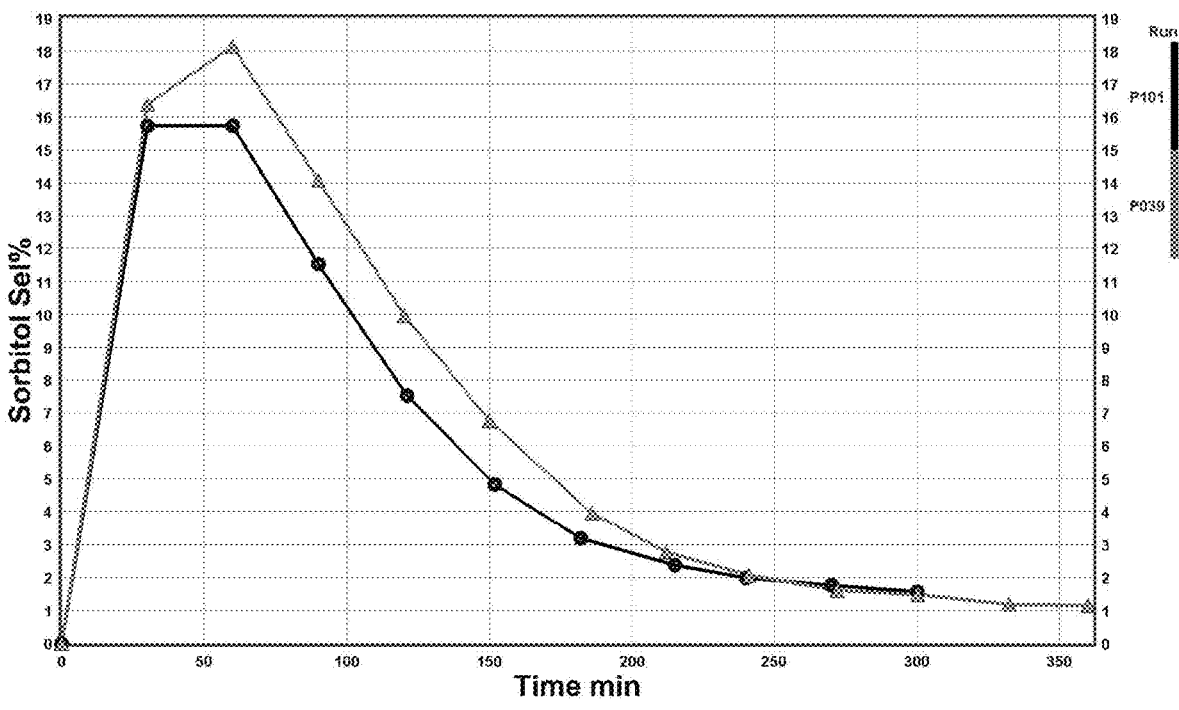
Figure 5 (closed circles relate to P101, closed triangles relate to P039)
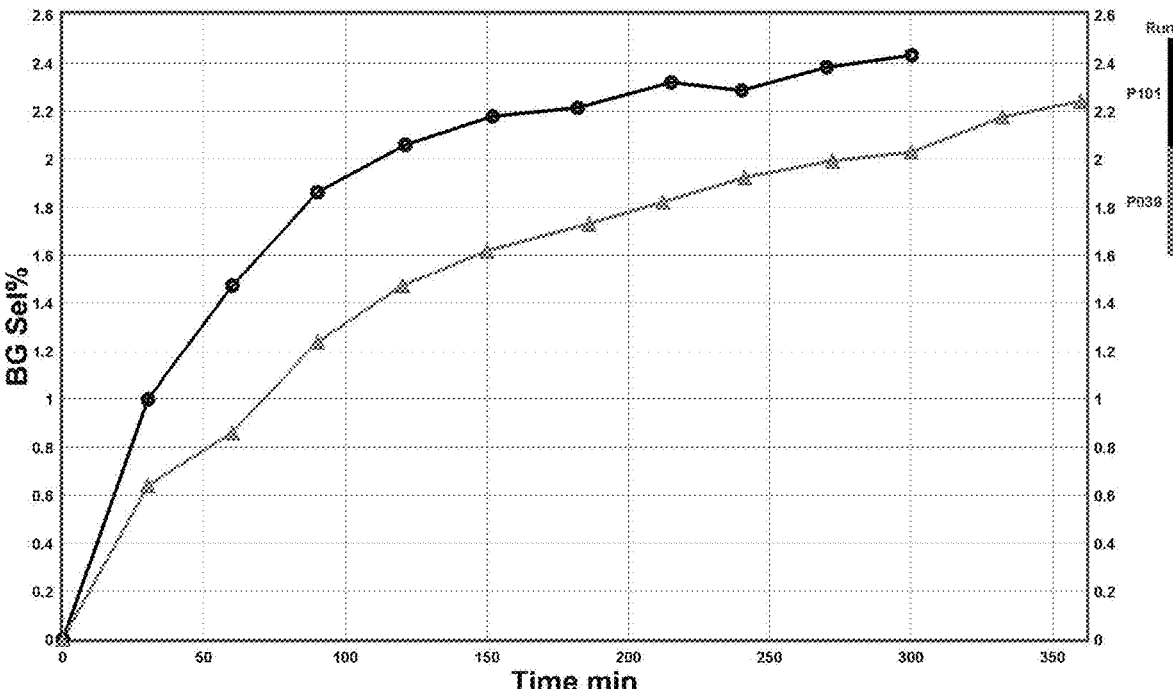
Figure 6 (closed circles relate to P101, closed triangles relate to P039)

PROCESS FOR RECOVERING AND REGENERATING A CATALYST FROM ASH

INTRODUCTION

The present invention relates to a process for recovering and regenerating a tungsten compound suitable as co-catalyst in converting carbohydrates with hydrogen into alkylene glycols and polyols, from ash comprising one or more tungsten-oxygen components (e.g. comprising a tungstate and/or tungstic acid). Such ash is obtainable from burning a liquid mixture comprising alkylene glycols and/or polyols and sodium tungstate and/or tungstic acid. The recovered and regenerated tungsten-component catalyst may be fed to a reactor in which it is a co-catalyst in hydrogenolysis of carbohydrates.

BACKGROUND OF THE INVENTION

WO 2016/114661 discloses a continuous process for preparation of ethylene glycol from a carbohydrate source. Said process is carried out in a stirred tank reactor (CSTR) in which a catalyst system is present. Said catalyst system comprises a tungsten compound and at least one hydrogenolysis metal. The hydrogenolysis metal is preferably present in the form of a catalyst supported on a carrier. Such heterogeneous catalyst particles can fairly easily be separated from the effluent stream e.g. by a sieve plate and added back. The tungsten compound on the other hand is generally present dissolved or dispersed in the liquid reaction medium (i.e. present as a homogenous catalyst compound) and not so easily removed from the effluent stream. Hence, the tungsten compound is partly removed as part of the effluent in operating the process in a CSTR. In order to maintain a desired concentration of the tungsten compound, it is thus needed that continuously or periodically the required tungsten compound is added to the reactor (next to carbohydrate source, diluent and hydrogen). This is what is done in the process of WO2016/114661.

The tungsten compound to be added may be a freshly prepared tungsten compound, or it may be a regenerated tungsten compound. A regenerated tungsten compound is more attractive for several reasons in the longterm, but it requires the tungsten compound that is dissolved or dispersed in the reactor effluent to be recovered, and subsequently regenerated. In such process, regeneration may be necessary as the tungsten compound found in the effluent may not necessarily be in the same physical or chemical composition as is desired for a most effective and/or selective reaction. Hence, both recovery of the tungsten compound from the effluent of the reaction in WO2016/114661 is desired, but also regeneration in a form that it is suitable again for feeding back to the reactor.

WO2017/042125 discloses that a bleed stream from a recycle loop, which bleed stream and recycle loop comprise hydrocarbon heavies and a homogeneous catalyst compound (containing a metallic compound) may be subjected to burning at a temperature of 300-750° C., to yield a solid residue. The bleeding is done to prevent build-up of heavy components that cannot be broken down to provide glycols, and that it also may prevent build-up of pollutants present in the saccharide feedstock. The bleed stream of the process allows for avoiding build-up of contaminants of organic nature, as these are burned. It is stated in WO2017/042125 that the solid residue, which contains compounds derived from the homogeneous catalyst, may be subjected to further processing. It is also stated that the metallic compound present in the residue (of the ash) may require reactivation. The sole example heats a stream of heavy hydrocarbons and sodium metatungstate catalyst in an oxygen-containing atmosphere to 450° C., to yield a white, water-soluble solid containing $Na_2W_2O_7$ and $Na_2WO_4$ which is stated to have comparable catalytic activity compared to fresh catalytic material fed to the reactor.

Burning a bleed stream in a process for producing ethylene glycol and/or propylene glycol in a continuous manner from a feed to a reactor system is indeed a convenient method to avoid the build-up of contaminants that can be burned, such as most organic contaminants like polyols or sugar alcohols. In case the ash of the process of WO2017/042125 is disposed of, indeed contaminants of inorganic nature are also removed (organic contaminants are removed by burning). However, if, like in the example of WO2017/042125 the solid material dissolved is re-used again as catalyst, the process does not remove contaminants of inorganic nature, such as sodium, calcium, magnesium, or salts thereof. Such ions may be detrimental to the desired reaction if excessive build-up is obtained.

Hence, there is a need for a process enabling recovery of part or all of the tungsten compound from the ash that can be obtained by burning (or subject to thermal decomposition and/or oxidation) of a bleed or side stream of a process for producing ethylene glycol and/or propylene glycol and/or glycerol, yet which process enables removal or reduction of inorganic contaminants. More in particular, the process should preferably allow for removal or reduction of (salts or oxides of) sodium, calcium, or magnesium. It is furthermore desired that the tungsten compound recovered is in a form that it can be used again in a process for producing ethylene glycol and/or propylene glycol and/or glycerol from carbohydrates using hydrogen and a catalyst system said catalyst system comprising a tungsten compound and a hydrogenolysis metal selected from the groups 8, 9 or 10 of the Periodic Table of Elements. Preferably, the tungsten compound rom the ash can be recovered, in a form that facilitates feeding back to the process.

SUMMARY OF THE INVENTION

It has now been found that the above objective can be achieved, at least in part, by a process for recovering and regenerating a tungsten compound suitable as co-catalyst in converting carbohydrates with hydrogen into alkylene glycols and polyols, from ash comprising one or more tungsten-oxygen components wherein said process comprises the steps of:

a. contacting the ash with an inorganic acid having a pH of below 2;

b. separating the mixture obtained from step a. in a solid fraction and a liquid fraction;

c. washing the solid fraction obtained by step b. with an aqueous liquid;

d. solubilising the washed solids obtained by step d. in an alkylene glycol composition and dissolving an alkali hydroxide in said alkylene glycol composition, wherein the amount of alkali hydroxide is chosen such that the molar ratio alkali hydroxide:tungstic acid in the resulting composition is between 0.2 and 2.

In the above process, the ash can be obtained by burning an effluent stream (or part thereof) of a reactor (e.g. operating in a continuous or semi-continuous manner) in which hydrogenolysis of carbohydrates like sugars is performed with hydrogen under pressure, and in the presence of a catalyst system, said catalyst system comprising a tungsten compound and a hydrogenolysis metal selected from the groups 8, 9 or 10 of the Periodic Table of Elements. Such reactions are set out in the prior art herein discussed. Such effluent stream can be the effluent after valuable components like ethylene glycol and/or propylene glycol and/or glycerol and/or others are removed from such effluent, e.g. by distillation. It can also be a bleed stream, with or without removing the valuable glycols set out above.

Hence, the invention further relates to a process for producing ethylene glycol and/or propylene glycol and/or glycerol in a continuous manner from a feed to a reactor system, the feed comprising hydrogen and a carbohydrate source in a diluent, the reactor system comprising a catalyst system, said catalyst system comprising a tungsten compound and a hydrogenolysis metal selected from the groups 8, 9 or 10 of the Periodic Table of Elements, wherein the flow out of the reactor system comprises diluent, a tungsten compound, one or more of ethylene glycol, propylene glycol, glycerol and one or more polyols with higher boiling points than ethylene glycol, wherein said flow out of the reactor system is subjected to the following process steps:

a. separating the flow out of the reactor by one or more distillation stages into ethylene glycol and/or propylene glycol and/or glycerol, and one or more bottom streams comprising polyols with higher boiling points than ethylene glycol and one or more tungsten compounds, b. subjecting a bottom stream comprising polyols with higher boiling points than ethylene glycol and one or more tungsten compounds of said distillation stages to a burner in which at least part of said polyols is burned, and at least part of the ash is recovered, c. contacting the recovered ash with an inorganic acid having a pH of below 2;

d. separating the mixture obtained from step c. in a solid fraction and a liquid fraction;

e. washing the solid fraction obtained by step d. with an aqueous liquid;

f. solubilising the washed solids obtained by step e. in an alkylene glycol composition and dissolving an alkali hydroxide in said alkylene glycol composition, wherein the amount of alkali hydroxide is chosen such that the molar ratio alkali hydroxide:tungstic acid in the resulting composition is between 0.2 and 2.

g. feeding at least part of the mixture obtained by step f. back to the reactor system.

In such process, the temperature in the reactor is typically between 120° and 300° C., and hydrogen partial pressure is typically between 1 and 6 MPa.

BRIEF DESCRIPTION OF THE DRAWINGS

FIG. 1 shows the mass balance of the experiments described in the Examples attained for tungsten-containing compound according to the invention (P101) for 300 minutes and for fresh tungsten-containing compound as a reference (P039) for 360 minutes.

FIG. 2 shows the ethylene glycol (EG) selectivity in the experiments described in the Examples for tungsten-containing compound according to the invention (P101) for 300 minutes and for fresh tungsten-containing compound as a reference (P039) for 360 minutes.

FIG. 3 shows the propylene glycol (PG) selectivity in the experiments described in the Examples for tungsten-containing compound according to the invention (P101) for 300 minutes and for fresh tungsten-containing compound as a reference (P039) for 360 minutes.

FIG. 4 shows the glycerol selectivity in the experiments described in the Examples for tungsten-containing compound according to the invention (P101) for 300 minutes and for fresh tungsten-containing compound as a reference (P039) for 360 minutes.

FIG. 5 shows the sorbitol selectivity in the experiments described in the Examples for tungsten-containing compound according to the invention (P101) for 300 minutes and for fresh tungsten-containing compound as a reference (P039) for 360 minutes.

FIG. 6 shows the butylene glycol (BG) selectivity in the experiments described in the Examples for tungsten-containing compound according to the invention (P101) for 300 minutes and for fresh tungsten-containing compound as a reference P039) for 360 minutes.

DETAILED DESCRIPTION OF THE INVENTION

"Continuous process" or "in continuous manner" is herein to be understood as not a batch process. It takes place in a reactor system with at least one feed, and one product stream, and is intended to run in steady state (after start-up). Duration (from start-up to stopping the reaction) is preferably at least 5 times the average residence time of the reactor system, more preferably at least 10 times the average residence time, most preferably at least 100 times the average residence time.

In the processes according to the present invention, the tungsten-oxygen components and tungsten compounds preferably comprises tungstic acid and/or an alkali tungstate, and in case of alkali tungstate such preferably comprises sodium tungstate and/or potassium tungstate. It says comprising, as often other tungsten-oxygen compounds (e.g. tungsten oxide) can be part of the tungsten co-catalyst used, either intentionally or because components are transformed into other tungsten-oxygen components.

In the processes according to the present invention, the inorganic acid to treat the ash has pH of below 2, preferably below 1.5, more preferably below 1. Said inorganic acid can be any suitable inorganic acid capable of giving an aqueous solution of pH below 2, and with presence of some water. Suitable examples encompass hydrochloric acid, sulphuric acid, phosphoric acid and nitric acid. It is preferred that the inorganic acid used in comprises hydrochloric acid. Preferably the inorganic acid to treat the ash is an aqueous solution of hydrochloric acid, and preferably such aqueous solution contains hydrochloric acid has a molarity of between 1 and 6 M, preferably between 1.2 and 4 M, more preferably between 1.5 and 3 M.

As to the amount of (aqueous) inorganic acid to treat the ash in the present invention, it is preferred that the weight ratio inorganic acid:ash is between 50:1 and 1:1. More preferably, such amount is between 30:1 and 2:1. Higher amounts are possible, but create difficulties in handling such and do not seem to provide further benefits.

In the processes according to the present invention, the step of separating the mixture obtained from the process step of the step acid-treatment in a solid fraction and a liquid fraction can be carried out by means known in the art of separating fine powders from (aqueous) liquids, such as centrifuging, decanting, filtration, and other techniques.

In the processes according to the present invention, the washing step that follows the above separation of solid and liquid matter is washing of the solid matter. This washing is carried out e.g. to remove most of the acid and dissolved salts and oxides. The washing car be carried out with an aqueous liquid, preferably water, preferably demineralized water. By employing successive wash steps the pH of the wash liquid increases. The number of wash steps is at least 1, preferably at least 2, preferably at least 3 steps. The amount of wash liquid used per cycle is preferably from 0.5 to 20 times the amount of acid used.

The effluent stream of the reactor in which hydrogenolysis of carbohydrates can take place, optionally after removing/isolating desired products such as ethylene glycol and/or propylene glycol, will contain polyols such as sorbitol, glycerol and erythritol. One or more of these polyols (e.g. glycerol) can also be worthwhile to isolate, depending on techniques, intended use and market prices. However, it may be practical to isolate products for which the value exceeds the cost of isolation in desired purity. This means that usually some polyols remain, of which it is not economical to isolate them. Such effluent from the reactor usually contains homogeneous co-catalyst based on tungsten. Such tungsten compound can be isolated first (prior to isolating desired glycols), but it can also stay in solution in the reactor products (containing the polyol/glycol mixture). In particular, when the tungsten based co-catalyst comprises tungstic acid such is found to stay dissolved in the polyols quite well. Thus, an effluent of such hydrogenolysis reaction in which the reactor contains tungstic acid as part of the tungsten-based co-catalyst may contain, next to polyols and desired glycols, tungstic acid. When such effluent us subjected to burning, e.g. to temperatures above 900° C., the organic molecules like polyols and glycols are 5 decomposed, leaving an ash comprising various inorganic components, mainly being oxides and salts. Such oxides and salts can be of tungsten, but such can also be of metals like sodium, potassium, calcium, magnesium, and others. Origin of such (non-tungsten) components can be e.g. the carbohydrates: some sugars contain some of these elements. It is generally preferred to avoid build-up of these non-tungsten salts and oxides, in particular with continuous processing, which this methods achieves, at least in part.

Hence, it may be preferred in the processes according to the present invention that the ash is obtainable (preferably obtained) from burning a liquid mixture comprising alkylene glycols and/or polyols as well as sodium tungstate and/or tungstic acid. As set out above, such mixture may be obtained directly from a reactor in which hydrogenolysis of carbohydrates with hydrogen is talking place, e.g. on the bleed stream 15 or part of the product stream, e.g. after obtaining desired alkylene glycols like ethylene glycol and/or propylene glycol and/or glycerol. The polyols in this connection generally comprise one or more of glycerol, sorbitol, erythritol. Glycerol in this connection can perform both as desired product, but not all glycerol need to be removed, it can suitably be used as vehicle to carry the used tungsten catalyst that exits the reactor with the product stream.

Following the above, it is preferred that the effluent subjected to burning can be a bleed stream or part thereof or it can be the product stream (of a hydrogenolysis of sugar reactor), after removal of desired products like ethylene glycol and/or propylene glycol.

In the processes according to the invention it is preferred that one or more tungsten-oxygen components of the ash comprises an alkali tungstate and/or tungstic acid. Other tungstated components may also be present, as under process conditions tungstic acid or tungstate may be converted into another tungsten-oxygen containing compound.

Without wishing to be bound by theory, the processes according to the invention, after treatment of the ash with acid and washing, give a solid that is believed to contain tungstic acid, possibly next to other tungstated species. Such solid tungstic acid may be used as co-catalyst compound in the hydrogenolysis reaction, but such solid is generally not easy to dose or apply. Hence, it is preferred to have such component dissolved or solubilized in a liquid that can be fed to the reactor, next to e.g. carbohydrates. It was found that such acid-treated, washed, ash can be solubilised or dissolved well in an alkylene glycol. In this connection, it is preferred that the alkylene glycol composition in which the acid treated, washed ash (i.e. the regenerated tungsten-component catalyst) is dissolved or solubilized comprises at least 50% by weight of ethylene glycol or propylene glycol, preferably it comprises at least 70% by weight of ethylene glycol. The advantage of such glycols is that they are also produced in the reaction, and hence no foreign solvent is added to the reaction mixture. Such alkylene glycol does not need to be a pure ethylene glycol or pure propylene glycol: it can also by a mixture of the two, optionally with other glycols being present. The alkylene glycol in which the regenerated catalyst is dissolved or solubilized may also be or comprise glycerol.

It was found that, in order to dissolve or solubilize the acid-treated, washed ash (i.e. the solid regenerated tungsten co-catalyst) in the alkylene glycol such is facilitated if some alkali hydroxide like sodium hydroxide or potassium hydroxide is present. Such alkali hydroxide may be added to the alkylene glycol in dry form, or as a solution in water. In this connection, it is preferred that the alkali hydroxide added to the alkylene glycol and the acid-treated, washed ash comprises sodium hydroxide, potassium hydroxide, or a mixture thereof. A preferred alkali hydroxide in this connection is sodium hydroxide.

It was found that dissolution or solubilizing the regenerated tungsten catalyst (the acid-treated, washed ash obtainable form burning part or all of the effluent of the reactions herein discussed) in alkylene glycol is best facilitated (and still gives good results in the hydrogenolysis reaction) when the amount of alkali hydroxide in step d. is such that the molar ratio alkali hydroxide:tungstic acid in the resulting composition is between 0.3 and 1.5, preferably between 0.4 and 1.2, more preferably between 0.5 and 1. Hence, these are preferred ratios for the molar ratio alkali hydroxide:tungstic acid in the resulting composition when solubilized or dissolved in the alkylene glycol.

It may be preferred that after dissolving or solubilizing the acid-treated, washed ash in alkylene glycol in the presence of some alkali hydroxide, that the composition so-obtained is subjected to filtration.

As an alternative, instead of dissolving the acid-treated, washed ash in alkylene glycol in the presence of some alkali hydroxide, the acid-treated, washed ash may be dried for solid storage. At any time suitable such dried regenerated catalyst may be dissolved or solubilized in alkylene glycol in the presence of alkali hydroxide as set out.

In the processes according to the present invention, it is preferred that the tungsten compound or tungsten-oxygen component suitable as co-catalyst in converting carbohydrates with hydrogen into alkylene glycols and polyols that is produced by the regeneration comprises tungstic acid. Preferably, such comprises at least 80% of tungstic acid, by weight based on the total tungsten-containing components.

Examples

Waste Stream Preparation

A model waste stream was prepared that contained various polyols, tungstic acid and some salts. This model waste stream was designed to look similar to a waste stream that can be obtained from experiments in making ethylene glycol and propylene glycol in a process similar to that reported in WO2016/114661. Such waste stream can be obtained after removal of water, lower alkanols like methanol and ethanol, and after removal by distillation of ethylene glycol and propylene glycol when carrying out the aforementioned process. The model waste stream had the composition as in table 1.

TABLE 1

| waste stream composition | |
|---|---|
| component | Weight % |
| Glycerol | 66 |
| Sorbitol | 14 |
| Erythritol | 10 |
| $H_2WO_4$ | 8 |
| NaOH | 1 |
| KOH | 0.042 |
| $CaCl_2$ | 0.005 |
| $Na_2SO_4$ | 0.106 |
| MgO | 0.001 |

Ash Preparation

This model waste stream was subjected to burning in a natural-gas fired flame (in presence of air) with a residence time of about 1 second, at a temperature of about 1200° C., in a burner with a downward direction so as to be able to collect ash particulates formed by burning. Three different runs were done, and ash was collected of several points of the burner. In total seven ash samples (varying from whitish to light grey in appearance, all fine particles) were assembled from these three runs and subjected to an elemental analysis with ICP (Inductively Coupled Plasma) technique. The results are in table 2, the ranges setting out the ranges found for each of the seven samples.

TABLE 2

| ash elemental composition | |
|---|---|
| Element | Wt % |
| W | 66-73 |
| O | 18-22 |
| Na | 5.6-7.5 |
| C | 3.5-6.1 |
| Ca | 0.05-0.17 |
| Mg | 0.02-0.1 |

One sample (3$^{rd}$ run, bottom of burner) the ash (light gray) the elemental analysis (C, O not measured) was as in table 3.

TABLE 3

| ash sample 3 bottom burner, elemental composition | |
|---|---|
| Element | Wt % |
| W | 68.7 |
| Na | 5.8 |
| Ca | 0.055 |
| Mg | 0.025 |

Regeneration of the Ash to Catalyst

The sample of ash of table 3 was combined with the sample (whitish) of run nr 3 collected at a different point in the burner equipment were combined and taken further for the rest of this experimental section. In total 9 g of this combined sample was mixed with 90 g of an aqueous hydrochloric acid solution (2 M) in an Erlenmeyer on a heating plate (with heating block for Ace tubes) heated to about 80° C. with reflux facility (set at about 10° C.), magnetic stirrer at 500 rpm. Duration after reaching the set temperature: 90 minutes. It was noted that although part of the ash dissolved in the aqueous acid, the majority of the ash did not dissolve. After cooling down, the mixture was centrifuged (Hettich Rotana 460, 4600 rpm, 5 minutes), the liquid was decanted and subjected to ICP elemental analysis. The result is set out in table 4 (percentage on amounts of table 3).

TABLE 4

| results elemental analysis decanted acid | |
|---|---|
| Element | Dissolution % |
| W | 3.34% |
| Na | 83.5% |
| Ca | 80.5% |
| Mg | 86.6% |

The elemental analysis of the acid means that most of the components containing sodium, calcium and magnesium in the ash of the model solution dissolve well in the acid after reflux, and that only a minor part of the tungsten-containing components in the ash of the model solution is lost with the acid.

The solid of the centrifuging treatment was washed with demi water (about 30 g water) and centrifuged again (4600 rpm, 5 minutes), decanted and the pH of the liquid measured. This washing was repeated to a total of 6 times. The pH of the washing liquid went up from about 0.75 from the first wash to about 3.4 for the last wash.

The washing water of the last wash was subjected to ICP elemental analysis on tungsten, the result was a dissolution percentage of 0.17%. This means little of the tungsten compounds from the ash is lost with the washing water.

The so-obtained (acid treated, and washed) ash was oven-dried for 14 hours at a temperature of about 80° C. and stored for later use.

The combined results on ICP elemental analysis for the aqueous hydrochloric acid used in the above and the wash water are set out in table 5 (percentage on amounts of table 3).

TABLE 5

| | results elemental analysis decanted acid and washing water | | |
|---|---|---|---|
| Element | Dissolution % - in acid treatment | Dissolution % - in water was | Dissolution % - in total |
| W | 3.35% | 0.17% | 3.5% |
| Na | 83.5% | — | 86.9% |
| Ca | 80.5% | — | 88.9% |
| Mg | 86.6% | — | 92.8% |

The results of table 5 show that due to acid treatment and subsequent washing most of non-tungsten metals in the ash are lost and most tungsten is maintained, as tungsten compounds.

The acid-treated, washed, and dried tungsten components from the ash were subject to dissolution in ethylene glycol, in the presence of some sodium hydroxide. For this, 6.7 g of the obtained acid-treated, washed and dried ash was mixed with 292.9 g of ethylene glycol and 1.41 g of sodium hydroxide solution (51% wt sodium hydroxide in water), resulting in a molar ratio NaOH/H$_2$WO$_4$ of 0.7. This was done in a glassware flask on a heating plate, with reflux column (open to the atmosphere) heated to about 150° C., 500 rpm, and once the set temperature was reached maintained for 120 minutes.

After cooling, the resulting mixture was filtered using vacuum filtration for removing minor undissolved residue. An ICP elemental analysis on tungsten yielded a dissolution of 84.2% as percentage of the boiler ash. The filtrate thus prepared was ready for use as co-catalyst in a process of converting sugars with hydrogen to glycols. The concentration of tungsten in the solution so obtained was also measured by ICP elemental analysis and turned out to be 1.26% (calculated as pure tungsten).

Use of the Regenerated Catalyst in Hydrogenolysis of Sugar

The ethylene glycol solution of the tungsten-containing compound so prepared (further containing sodium hydroxide and a minor amount of water) was used as co-catalyst in a hydrogenolysis experiment.

To this end, two experiments were conducted, one with the tungsten-compound contained in the ethylene glycol as obtained above, and one reference using a 5 weight % solution of fresh tungstic acid (H$_2$WO$_4$) in ethylene glycol. Both experiments were carried out using sucrose as carbohydrate.

The trials were carried out using the following reactor system.

The reactor was a 200 ml hastelloy autoclave, modified to a CSTR (Continuous Stirred Tank Reactor). Liquid feed (sugar in water, ethylene glycol, ethylene glycol containing tungstic acid and sodium hydroxide) and gas feed were fed separately into the reactor.

The effective liquid volume of the reactor was set to 148 ml. Liquid feed was fed to the reactor by an HPLC pump, nitrogen (for flushing prior to reaction) and hydrogen gas were fed via mass flow controllers. The reactor was stirred with a radial blade, hollow shaft stirrer. The outgoing line to the effluent capture vessel was fitted with a 20 μm stainless steel filter (to keep ruthenium catalyst particles in the reactor).

The reactor was pressurized by a backpressure regulator on the outgoing line (to only let liquids/gasses pass once a threshold pressure is overcome, e.g. if the BPR is set for 60 bar, it will only let materials pass once the reactor has surpassed 60 bar).

Nominal Parameters Set for Experiment:

Liquid flow: 5-7 ml/min

Gas flow 2 L/min

Reactor pressure: 65-80 bar

Heterogeneous catalyst loading: 5-9 gram Ruthenium (5%) on active carbon support (moisture content 50 wt %)

Stirring speed: 900 RPM

The trials carried out were code P101 (according to the invention) and P039 (comparison), with feeds and catalyst as set out in table 6.

TABLE 6

| | hydrogenolysis trials | |
|---|---|---|
| | P101 (acc. to invention) | P039 (reference) |
| Sucrose (g) | 340.3 | 390 |
| Water (g) | 1033.5 | 1180.9 |
| Homogeneous tungsten catalyst | 294.4 g of EG with dissolved therein ash as obtained as above, in amount equivalent to 1.26 wt % of tungsten as determined by ICP*, further containing NaOH | 117 g of a solution of 5 wt % of fresh tungstic acid in EG |
| EG (g) | 33.2 | 262.1 |
| 50 wt % NaOH solution (ml) | | 0.91 |

EG: ethylene glycol

*as the amount of tungstic acid in the ash cannot be determined directly: ICP gives the amount of pure tungsten The above resulted in the initial concentrations in the reactor as in table 7.

TABLE 7

| | hydrogenolysis trials - concentrations | |
|---|---|---|
| | P101 (acc. to invention) | P039 (reference) |
| Sucrose (wt %) | 20 | 20 |
| Water (wt %) | 60.7 | 60.6 |
| H$_2$WO$_4$ (wt %) | 0.34 | 0.30 |
| EG (wt %) | 19.0 | 19.1 |
| NaOH solution (g/L) | 0.41 | 0.35 |
| Weight ratio NaOH/H$_2$WO$_4$ | 0.12 | 0.12 |
| Molar ratio NaOH/H$_2$WO$_4$ | 0.73 | 0.73 |

EG: ethylene glycol

The experiments were conducted for 300 minutes (P101) and 360 minutes (P039).

The flow out of the reaction was analysed on levels of ethylene glycol, propylene glycol, butanediol, sorbitol. The results are expressed as mass balance and compound selectivity (the latter for ethylene glycol, propylene glycol, 1,4-butanediol, and sorbitol). Mass balance and compound selectivity are herein defined as:

Mass balance (%)=100×(sum of all compounds– cosolvent input)/sugar input

Compound selectivity (%)=100×(cosolvent output– cosolvent input)/sugar input

The results are set out graphically in FIGS. 1-6 (line with closed circles relates to P101, line with closed triangles relates to P039).

The invention claimed is:

1. A process for recovering and regenerating a tungsten compound suitable as co-catalyst in converting carbohydrates with hydrogen into alkylene glycols and polyols, from ash comprising one or more tungsten-oxygen components wherein said process comprises the steps of:

a. contacting the ash with an inorganic acid having a pH of below 2;

b. separating the mixture obtained from step a. in a solid fraction and a liquid fraction;

c. washing the solid fraction obtained by step b. with an aqueous liquid; and d. solubilising at least a part of the washed solids obtained by step c. in an alkylene glycol composition and dissolving an alkali hydroxide in said alkylene glycol composition, wherein the amount of alkali hydroxide is chosen such that the molar ratio alkali hydroxide: tungstic acid in the resulting composition is between 0.2 and 2.

2. The process according to claim 1, wherein the inorganic acid in step a. has a pH of below 1.

3. The process according to claim 1, wherein the inorganic acid in step a. comprises hydrochloric acid.

4. The process according to claim 3, wherein the inorganic acid in step a. comprises hydrochloric acid in a concentration of between 1 and 6 M.

5. The process according to claim 1, wherein the amount of inorganic acid in step a. is such that the weight ratio inorganic acid:ash is between 50:1 and 1:1.

6. The process according to claim 1, wherein the one or more tungsten-oxygen components of the ash comprises an alkali tungstate and/or tungstic acid.

7. The process according to claim 1, wherein the alkali hydroxide added in step d. comprises sodium hydroxide, potassium hydroxide, or a mixture thereof.

8. The process according to claim 1, wherein the amount of alkali hydroxide in step d. is such that the molar ratio alkali hydroxide:tungstic acid in the resulting composition is between 0.3 and 1.5.

9. The process according to claim 1, wherein the alkylene glycol composition in step d. comprises at least 50% by weight of ethylene glycol or propylene glycol.

10. The process according to claim 1, wherein the ash is obtainable from burning a liquid mixture comprising alkylene glycols and/or polyols as well as sodium tungstate and/or tungstic acid.

11. The process according to claim 1, wherein the polyols comprise one or more of glycerol, sorbitol, erythritol.

12. The process according to claim 1, wherein the tungsten compound suitable as co-catalyst in converting carbohydrates with hydrogen into alkylene glycols and polyols that is produced by the regeneration comprises tungstic acid.

\* \* \* \* \*